US00PP26743P2

(12) United States Plant Patent
Martinez

(10) Patent No.: US PP26,743 P2
(45) Date of Patent: May 17, 2016

(54) *HOSTA* PLANT NAMED 'MINI SKIRT'

(50) Latin Name: ***Hosta* hydrid (Tratt.)**
Varietal Denomination: Mini Skirt

(71) Applicant: Maria M Martinez, Fennville, MI (US)

(72) Inventor: Maria M Martinez, Fennville, MI (US)

(73) Assignee: Walters Gardens, Inc., Zeeland, MI (US)

( * ) Notice: Subject to any disclaimer, the term of this patent is extended or adjusted under 35 U.S.C. 154(b) by 241 days.

(21) Appl. No.: 13/999,271

(22) Filed: Feb. 5, 2014

(51) Int. Cl.
*A01H 5/12* (2006.01)

(52) U.S. Cl.
USPC ..... Plt./353

(58) Field of Classification Search
USPC ..... Plt./353
See application file for complete search history.

(56) References Cited

PUBLICATIONS

Perennial Resource retrieved on Nov. 18, 2015, retrieved from the Internet at <http://www.perennialresource.com/encyclopedia/view/?plant=2427> 3 pp.*

Plant Lust retrieved on Nov. 18, 2015, retrieved from the Internet at <http://plantlust.com/plants/hosta-mini-skirt/> 2 pp.*

Karin Walters, Walters Gardens, Inc. Wholesale Catalog Summer 2014-Spring 2015, Jul. 2014, front cover and p. 132, Walters Gardens, Inc., Zeeland, Michigan, US.

Walters Gardens, Inc. first sales of *Hosta* 'Mini Skirt', computer printout from search 2013/2014, one page.

Tony Avent, Plant Delights Nursery, Inc. 2014 Spring Sales Catalog & Plant Owner's Manual, front cover and p. 3, Plant Delights Nursery, Inc., Raleigh, North Carolina, US.

http://www.plantdelights.com/Hosta-Mini-Skirt-PPAF-for-Sale/Buy-Plantain-Lily/, Plant Delights Nursery, Inc. website, pp. 1-2. 2015.

Karin Walters, The Perennal Press from Walters Gardens, Inc., Nov. 1, 2013, front cover, Zeeland, Michigan, US. one page.

* cited by examiner

*Primary Examiner* — June Hwu

(57) ABSTRACT

A new and distinct *Hosta* plant named 'Mini Skirt' with coarsely-sinuate cordate leaf blades having variegation of creamy yellow to creamy white margins and dark green center and feathering intermediate colors. The plant habit is short, compact and rounded with flowering just above foliage, and the leaves and scapes are thick substance and stiff.

1 Drawing Sheet

Botanical classification: *Hosta* hybrid (Tratt.).
Variety denomination: 'Mini Skirt'.

BACKGROUND AND ORIGIN OF THE PLANT

The present invention relates to a new and distinct *Hosta* plant, *Hosta* 'Mini Skirt' hereinafter also referred to as the new plant or just the cultivar name, 'Mini Skirt'. *Hosta* 'Mini Skirt' was discovered by Maria Martinez as a non-induced, naturally-occurring, whole-plant mutation in a batch of tissue cultured *Hosta* 'Mighty Mouse' (not patented) at a nursery greenhouse in Zeeland, Mich., USA during the summer of 2008. The new plant has been asexually propagated by division at the same nursery in Zeeland, Mich. USA since 2009 and also by careful shoot tip plant tissue culture with the resultant asexually propagated plants having retained all the same traits as the original plant. 'Mini Skirt' is stable and reproduces true to type in successive generations of asexual reproduction.

*Hosta* 'Mini Skirt' has not been made publically available or sold anywhere in the world prior to the filing of this application. Any public disclosure of 'Mini Skirt' has been by the inventor, or one who obtained the material either directly or indirectly from the inventor, and any such disclosure has not been made more than one year prior to the application of this invention.

There are over 4,500 registered *Hostas* with The American *Hosta* Society, which is the International Cultivar Registration Authority for the genus *Hosta*. *Hosta* 'Mini Skirt' is a sport from 'Mighty Mouse' (not patented) which is one of many sports from *Hosta* 'Blue Mouse Ears' (not patented). The most similar *Hosta* cultivar known to the applicant is *Hosta* 'Mighty Mouse'. The new plant differs from 'Mighty Mouse' in that the margin appears wider but most notably in the course wave in the leaf bland, whereas 'Mighty Mouse' has a flat leaf blade. Another cultivar, 'Ruffled Mouse Ears' (not patented), has similar sport history, both originally arising from 'Blue Mouse Ears'. 'Ruffled Mouse Ears' has a similar coarse wave to the leaves but is not variegated. *Hosta* 'Pure Heart' (not patented) is a sport of 'Blue Mouse Ears' with foliage having a white center and green margin, but 'Pure Heart' also has a flatter leave than 'Mini Skirt' and variegation in a reverse pattern. *Hosta* 'Mouse Tracks' (not patented) is another sport of 'Blue Mouse Ears' with creamy streaking variegation throughout the dark green foliage and without a wide creamy white to creamy yellow margin. *Hosta* 'Mouse Tracks' also has a flatter leaf than 'Mini Skirt'.

Other *Hosta* cultivars have short habit and variegation of a similar nature, or other individual traits similar to 'Mini Skirt' but the new plant differs from the above cultivars and all other *Hostas* known to the applicant, by the combination of the following traits.

1. Coarsely-sinuate cordate leaf blades.
2. Leaves with creamy yellow to creamy white margins and dark green center and feathering intermediate colors.
3. Short, compact, rounded habit with flowering just above foliage.
4. Stiff scapes and leaves with thick substance.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

The drawing shows a three-year old plant in a container in mid-season grown in a shaded greenhouse at a nursery in Zeeland, Mich. with supplement fertilizer and water as needed.

DETAILED BOTANICAL DESCRIPTION

The following descriptions and color references are based on the 2001 edition of The Royal Horticultural Society Colour Chart except where common dictionary terms are used. The new plant, *Hosta* 'Mini Skirt', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with and supplemental water and fertilizer.

Botanical classification: *Hosta*×hybrid.

Parentage: Whole-plant mutation of *Hosta* 'Mighty Mouse' (not patented).

Propagation: Garden division and sterile plant tissue culture.

Time to initiate roots from tissue culture: About two to three weeks.

Growth rate: Moderate.

Crop time: About 10 to 12 weeks to finish during the summer in a one-liter container from rooted tissue culture plantlet.

Rooting habit: Fleshy, lightly branching.

Plant shape and habit: Hardy herbaceous perennial with basal rosette of leaves emerging from rhizomes producing a short symmetrical mound of broadly horizontal leaves.

*Plant size*.—Foliage height 9.0 to 12.0 cm above soil line to the top of the leaves and about 24.0 to 28.0 cm wide at the widest point just above soil line.

Foliage description: Entire, glabrous, glaucous above and below but more glaucous below, cordate, broadly acute leaf apex with cordate base; coarsely sinuate.

Leaf blade: About 6.0 cm long and 6.0 cm wide; dark green center and light yellow margin that varies in width from 8.0 mm to 20.0 mm wide at broadest portion of leaf blade; surface smooth without dimpling, bulging or blistering.

*Leaf blade color*.—Early season shortly after emergence adaxial (top) center color more green than RHS 122A and more blue than RHS N138C; early season adaxial margin lighter and more yellow than RHS N144D and more green than RHS 154B; early season abaxial (underside) center nearest RHS N138D; early season abaxial margin between RHS 1C and RHS 11B; other intermediate colors in irregular patches and stripes between the margin and center portions on both adaxial and abaxial sides nearest RHS 138C, RHS 144C and RHS 138D; mid-season and later summer adaxial centers nearest RHS 137A; mid-season and later adaxial margins nearest RHS 160D; mid-season and later abaxial center nearest RHS N138D; mid-season and later abaxial margins nearest RHS 11D; intermediate colors where adaxial margin and center unevenly and irregularly fold over each other include: more green than RHS 160B and nearest RHS 3C, nearest RHS 148C, between RHS 147B and between RHS 147C and nearest 145B; irregular intermediate abaxial colors of nearest RHS 138B, lighter than RHS N138D and nearest RHS 145A.

Petiole: Entire, glabrous concavo-convex; mostly straight from base of plant to leaf base with little bending or curving, stiff; 4.0 to 6.0 cm long and 5.0 to 6.5 mm wide at base, average about 5 cm long and 5.5 mm wide.

*Petiole color*.—Adaxial centers nearest RHS 137C; adaxial margins nearest RHS 157C; abaxial center nearest RHS N138C; abaxial margins nearest RHS 157D.

Veins: Parallel, raised on abaxial side, normally 8 pairs and one main center vein.

*Veins color*.—Adaxial and abaxial veins the same color as the surrounding tissue.

Flower description:

*Buds one day prior to opening*.—Globose with rounded apex and narrow base; about 1.8 cm in diameter with base narrowing at about mid-length to about 0.4 cm diameter; about 3.5 cm long.

*Bud color*.—Between RHS 85B and RHS 91B with stripes of nearest RHS 85D.

*Flowers*.—Perfect; perianth shape funnelform; held nearly horizontal with pedicel at 90 degree angle to peduncle; corolla tube about 3.0 cm wide and 4.0 cm long, (distal flowers smaller), persists for a normal period, usually one day on plant or as cut flower; scapes remain effective with flowers from late June to mid-July with 20 to 25 flowers per scape; no detectable fragrance.

*Tepal*.—Two identical sets of three, glabrous, entire; fused at base; clavate with broadly acute apex; each approximately 3.5 cm long and 1.4 cm wide.

*Tepal color*.—Coloring of both sets identical; abaxial basal one third white, lighter than RHS 155D; abaxial center and distal portion nearest RHS 85D with three main veins nearest RHS 85C; adaxial basal one quarter white, lighter than RHS 155D; adaxial distal three quarters nearest RHS N82D with three main veins of between RHS N82B and RHS N82C and one side vein on either side of the three main veins nearest RHS N82C.

Gynoecium: Single.

*Style*.—Single, approximately 4.3 cm long, 1.5 mm diameter, curved upward slightly in distal 1.0 cm; color lighter than RHS 155D.

*Stigma*.—Globose, about 2 mm in diameter, lighter than RHS 157D and slightly more yellow-green than RHS 155D.

Androecium:

*Filaments*.—Six, approximately 4.0 cm long and 1.0 mm in diameter; curved upward to nearly 90 degrees in the apical 1.0 cm; color lighter than RHS 155D.

*Anthers*.—Elliptic; dorsifixed, dehiscent longitudinally; about 2.5 to 3.5 mm long, 1.5 mm wide; color between RHS N187A and RHS N186B.

*Pollen*.—Elliptic, less than 0.1 mm long, color nearest to RHS 14C.

Peduncle: Usually one per mature division; glaucous, glabrous; nearly vertical to slightly curved up to 20 degrees from vertical, more curved with horizontal or one directional lighting, more erect or vertical with even and overhead lighting; 18 to 24 cm tall, and up to 9 mm in diameter at base.

*Peduncle color*.—Nearest RHS N138D in the lower portion and nearest RHS 138B in the upper portion.

Pedicel: Short, glabrous; approximately 5 mm long, 2 mm diameter; nearest RHS 138C with tinting of nearest RHS 85C where exposed to more light.

Scape bracts: Each flower normally subtended by a single bract, decreasing in size distally with one or two below first flowers; bracts subtending flowers protruding to nearly perpendicular to scape; concaved supporting flower bud; lowest bracts resembling sessile leaves with largest 2.5 cm long 6.0 cm wide, first bract subtending flower about 12 mm long and 5 mm wide.

*Scape bract color*.—Adaxial center between RHS 138D and RHS N138B, adaxial and abaxial margin more yellow than RHS 145C and more green than RHS 11C; abaxial centers between RHS 138B and RHS N138C.

Fruit: Not yet observed.

Seed: Not yet observed; infrequent or sterile under present growing conditions.

Disease resistance: The new plant has not shown any resistance to pests and diseases common to *Hostas*. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *Hostas*.

I claim:

1. A new and distinct ornamental plant cultivar named *Hosta* 'Mini Skirt' as herein described and illustrated.

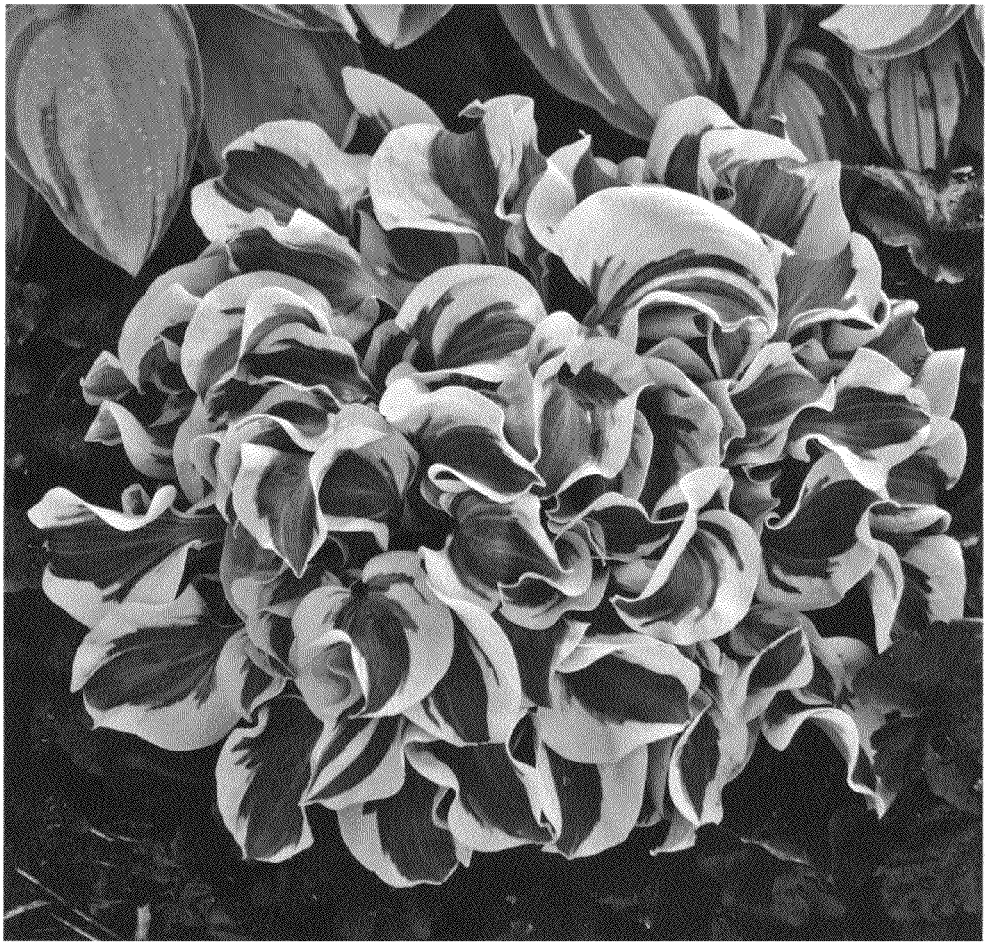

* * * * *